United States Patent
Young et al.

(10) Patent No.: US 7,905,915 B2
(45) Date of Patent: Mar. 15, 2011

(54) Z-STENT WITH INCORPORATED BARBS

(75) Inventors: Ronan T. Young, Spencer, IN (US); Christopher G. Dixon, Bloomington, IN (US)

(73) Assignee: Cook Incorporated, Bloomington, IN (US)

(*) Notice: Subject to any disclaimer, the term of this patent is extended or adjusted under 35 U.S.C. 154(b) by 32 days.

(21) Appl. No.: 12/342,670

(22) Filed: Dec. 23, 2008

(65) Prior Publication Data

US 2009/0171442 A1 Jul. 2, 2009

Related U.S. Application Data

(60) Provisional application No. 61/017,078, filed on Dec. 27, 2007.

(51) Int. Cl.
*A61F 2/06* (2006.01)
(52) U.S. Cl. ..................................... 623/1.36
(58) Field of Classification Search .................. 623/1.36
See application file for complete search history.

(56) References Cited

U.S. PATENT DOCUMENTS

| | | | |
|---|---|---|---|
| 5,662,700 A * | 9/1997 | Lazarus ........................ 606/194 |
| 5,720,776 A * | 2/1998 | Chuter et al. ................. 623/1.36 |
| 5,800,515 A | 9/1998 | Nadal et al. |
| 5,897,589 A | 4/1999 | Cottenceau et al. |
| 5,902,334 A * | 5/1999 | Dwyer et al. ................. 606/194 |
| 6,042,605 A | 3/2000 | Martin et al. |
| 6,200,336 B1 | 3/2001 | Pavcnik et al. |
| 6,221,102 B1 | 4/2001 | Baker et al. |
| 6,355,056 B1 | 3/2002 | Pinheiro |
| 6,395,022 B1 | 5/2002 | Piplani et al. |
| 6,540,778 B1 | 4/2003 | Quiachon et al. |
| 6,589,275 B1 | 7/2003 | Ivancev et al. |
| 6,962,604 B2 | 11/2005 | Hijlkema |
| 7,081,132 B2 * | 7/2006 | Cook et al. .................... 623/1.36 |
| 7,118,594 B2 * | 10/2006 | Quiachon et al. ............ 623/1.35 |
| 7,147,660 B2 | 12/2006 | Chobotov et al. |
| 7,166,125 B1 * | 1/2007 | Baker et al. .................... 623/1.36 |
| 2002/0091439 A1 | 7/2002 | Baker et al. |
| 2003/0236570 A1 | 12/2003 | Cook et al. |
| 2004/0260383 A1 | 12/2004 | Stelter et al. |
| 2005/0015141 A1 | 1/2005 | Quiachon et al. |
| 2006/0116751 A1 * | 6/2006 | Bayle et al. .................. 623/1.16 |
| 2006/0178732 A1 | 8/2006 | Chobotov et al. |
| 2010/0057195 A1 * | 3/2010 | Roeder et al. ................ 623/1.35 |

FOREIGN PATENT DOCUMENTS

EP 839 505 A1 5/1998
WO WO 2004/105852 A1 12/2004

* cited by examiner

*Primary Examiner* — Brian E Pellegrino
*Assistant Examiner* — Jacqueline Woznicki
(74) *Attorney, Agent, or Firm* — Brinks Hofer Gilson & Lione

(57) ABSTRACT

A stent constructed from at least two individual monolithic stent units is provided. The stent includes at least two individual stent units. Each individual stent unit has, as a monolithic structure, a first strut, a second strut, and a third strut. A first apex adjoins the first and second struts, and a second apex adjoining the second and third struts, where the second apex is disposed in a direction generally opposite the first apex. The monolithic stent unit includes an attachment mechanism at the end of at least the first strut. The first strut of each monolithic stent unit is joined at an attachment point to the third strut of an adjacent monolithic stent unit. The attachment mechanism is bent to form an angle relative to the attachment point. A method of manufacturing the same stent also is provided.

19 Claims, 13 Drawing Sheets

Z-STENT WITH INCORPORATED BARBS

This application claims the benefit of priority from U.S. Provisional Application No. 61/017,078, filed Dec. 27, 2007, which is incorporated by reference.

BACKGROUND

This invention relates to endoluminal medical devices for implantation within the human or animal body for treatment of endovascular disease. In particular, this invention relates to stents for use with endoluminal medical devices having a novel attachment structure.

The functional vessels of human and animal bodies, such as blood vessels and ducts, occasionally weaken or even rupture. For example, the aortic wall can weaken, resulting in an aneurysm. One surgical intervention for weakened, aneurismal, or ruptured vessels involves the use of stent grafts to replace or repair the vessel. Stent grafts may be formed from a tube of a biocompatible material in combination with one or more stents to maintain a lumen therethrough. The stents are attached to the graft material in a number of ways, including by suturing the stent to the graft material.

It is preferable that these prostheses seal off the failed portion of the vessel. For weakened or aneurismal vessels, even a small leak in the prosthesis may lead to the pressurization of or flow in the treated vessel, which aggravates the condition the prosthesis was intended to treat. A prosthesis of this type can, for example, treat aneurysms of the abdominal aortic, iliac, or branch vessels such as the renal arteries.

The above-described examples are only some of the applications in which endoluminal devices are used by physicians. Many other applications for endoluminal devices are known and/or will be developed in the future. For example, in addition to the use of stents and stent-grafts to treat vascular stenosis and aneurysms, similar procedures may also be used to deploy vascular filters, occluders, artificial valves and other endoprosthetic devices.

Migration of endoluminal devices from their location of implantation may present a significant problem where the prosthesis is subject to the forces of blood flow, especially on the arterial side. For example, the prevention of migration is extremely important and challenging when placing a stent graft to repair an abdominal aortic aneurysm (AAA) where downstream migration of the device can result in the aneurysm no longer being excluded. Unlike surgically placed grafts that are sutured into place, only the radial forces of the stent are available to hold the prosthesis into place. If the aneurysm is no longer intact or subsequent rupture occurs, consequences may be dire.

To alleviate or obviate migration, attempts have been made to secure the device in place with a series of barbs or hooks that extend outward from the main body of the device, typically at its proximal end, either by attaching them to the stent frame with solder or by some other bonding technique, or to the graft material, typically by suturing. These barbs can be attached to the stent wire by wrapping, chemical bonding, welding, brazing, soldering or other techniques. For example, one embodiment of WO98/53761 utilizes barbs that extend from the suprarenal fixation stents to engage the aorta wall.

It has been observed that sutures attaching barbed stents to the graft material are subject to breakage due in part to the flexibility of the graft material and the considerable pulsatile forces of arterial blood acting on the device. These forces have been known to directly contribute to the detachment between the graft portion and anchoring stent.

It has also been observed that barbs separately attached to the stent frame are subject to fracture, detachment, or other failure, especially when the forces become concentrated at a particular location along the stent graft. Simply making the barbs stronger to prevent fracture can result in increased damage to the anchoring tissue. Furthermore, adding rigidity to any outward-projecting barbs may compromise the ability of the device to be compressed and loaded into a delivery system. The use of multiple barbs can prevent undesirable migration of the device, especially if there are a very limited number of barb failures. Yet, while a single barb failure should not result in the migration of the device and may not represent a problem clinically, barb fracture or failure is nevertheless currently classified as an adverse event that manufacturers seek to avoid.

Another solution to the problem of barb failure better was disclosed in U.S. Pat. No. 7,081,132 to Cook et al. There, the barb included a basal portion that joins the strut of the prosthesis from which the barb extends, and a stress-dispersing region located between the anchoring portion and the basal portion, usually closely adjacent to the basal portion, that is adapted to better distribute stresses and strain caused by forces acting on the barb, thus preventing their concentration at a particular point which would increase the likelihood of barb fracture. The stress-dispersing region may comprise a coil of a greater pitch than the windings of the basal portion, a coiled loop bend, U-shape bend, or other series of bends. However, this barb design still requires the use of a separate wire portion soldered, welded, or mechanically attached to the strut of a stent.

Typically, stents are manufactured from a single piece of material, and they are sized depending on the size of the vasculature of the patient receiving the stent. However, the process for creating the stent is time-consuming and makes it more difficult to cater to different patient sizes.

Accordingly, there remains a significant and unsolved need for a barb configuration that reduces barb failure and has a simple structure that does not require attaching a separate barb structure to the strut of the stent.

BRIEF SUMMARY

The present invention provides stent and a method of forming a stent. In particular, the invention provides a stent assembled from a series of individual monolithic stent units having incorporated barbs.

In one example, a stent includes at least two individual stent units. Each individual stent unit is a monolithic structure having a first strut, a second strut, and a third strut. A first apex adjoins the first and second struts, and a second apex adjoining the second and third struts, where the second apex is disposed in a direction generally opposite the first apex. The monolithic stent unit also includes an attachment mechanism at the end of at least the first strut. The first strut of each monolithic stent unit is joined at an attachment point to the third strut of an adjacent monolithic stent unit. The attachment mechanism is bent to form an angle relative to the attachment point.

In another example, a stent includes a series of at least two individual monolithic stent units including a first monolithic stent unit and a last monolithic stent unit in the series of stent units. Each stent unit is a monolithic structure that includes a first strut, a second strut, and a third strut. A first apex adjoins the first and second struts, and a second apex adjoining the second and third struts, where the second apex is disposed in a direction generally opposite the first apex. The monolithic stent unit also includes an attachment mechanism at the end of the first strut. The first strut of each monolithic stent unit is joined at an attachment point to the third strut of an adjacent monolithic stent unit. The attachment mechanism is bent to form an angle relative to the attachment point.

In another example, a method of forming a stent from a series of separate and individual monolithic stent units is provided. The method includes providing at least two individual monolithic stent units, then bending each of the monolithic stent units to form a configuration having three struts, a first strut, a second strut, and a third strut. A first apex adjoins the first and second struts and a second apex adjoins the second and third struts, and the second apex is disposed in a direction generally opposite the first apex. A portion of the first strut of each monolithic stent unit is attached to the third stent of an adjacent monolithic stent unit to join with the adjacent monolithic stent unit to form an attachment mechanism. Each attachment mechanism is bent to form an angle relative to the longitudinal axis of the second strut.

A stent constructed in the manner of the present invention provides an improved and easy to manufacture stent incorporating a stable and reliable attachment mechanism suitable for deployment within the body passageway of a patient. The individual monolithic stent units are simple units, and therefore, easily manufactured. The stent is also able to be readily sized for individual patients, because the size of the stent is based on the number and size of the individual monolithic stent units that are used to form the stent. Furthermore, the stent of this invention has monolithic stent units comprising attachment mechanisms at the end of at least one strut, eliminating the need to attach a separate attachment mechanism and making the manufacturing process simpler.

A stent constructed using an individual monolithic stent unit having the first strut of each individual monolithic stent unit and the third strut of an adjacent individual monolithic stent unit interconnected by laser welding, brazing, soldering, or ultrasonic welding has the advantage of securely attaching each individual monolithic stent unit to an adjacent individual monolithic stent unit.

A stent constructed using an individual monolithic stent unit having a coiled end preserves the radial force of the device, such that the inserted wire may be free to rotate within the lumen of the coil in which it is inserted. The freedom of movement creates less stress while the stent is in a collapsed configuration during delivery. The method of manufacturing the stent of the present invention additionally has the advantages of simple construction, as well as requiring no welding or soldering in order to affix the barbs. However, welding or soldering may be employed in order to further reinforce the attachment. The mechanical construction eliminates a point of weakness in the stent, which if broken, can cause displacement of the stent.

These and other features, aspects, and advantages will become better understood with regard to the following detailed description, appended claims and accompanying drawings.

BRIEF DESCRIPTION OF THE DRAWINGS

The components in the figures are not necessarily to scale, emphasis instead being placed upon illustrating the principles of the invention. Moreover, in the figures, like referenced numerals designate corresponding parts throughout the different views.

DETAILED DESCRIPTION OF THE DRAWINGS

Figure 1:
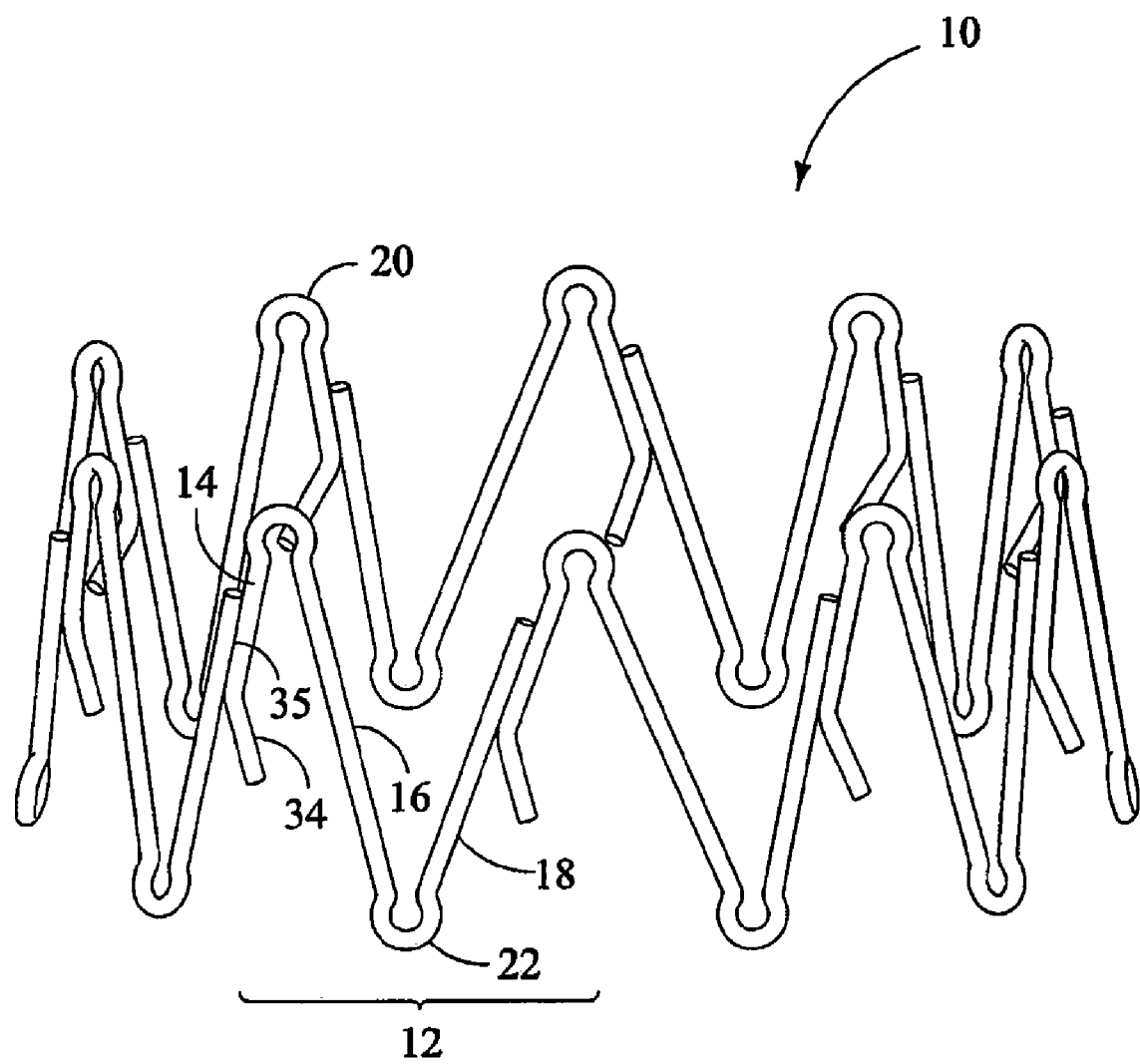
FIG. 1 shows an embodiment of a generally circular stent constructed from individual monolithic stent units according to the present invention.

Unless defined otherwise, all technical and scientific terms used herein have the same meaning as commonly understood to one of ordinary skill in the art to which this invention belongs.

The term "prosthesis" means any replacement for a body part or function of that body part. It can also mean a device that enhances or adds functionality to a physiological system.

The term "endoluminal" refers to or describes objects that can be placed inside a lumen or a body passageway in a human or animal body. A lumen or a body passageway can be an existing lumen or a lumen created by surgical intervention. As used in this specification, the terms "lumen" or "body passageway" are intended to have a broad meaning and encompasses any duct (e.g., natural or iatrogenic) within the human body and can include a mechanism selected from the group comprising: blood vessels, respiratory ducts, gastrointestinal ducts, and the like. "Endoluminal device" or "endoluminal prosthesis" thus describes devices that can be placed inside one of these lumens.

The term "stent" means any device or structure that adds rigidity, expansion force or support to a prosthesis. A stent is used to obtain and maintain the patency of the body passageway while maintaining the integrity of the passageway. In addition, the stent may be used to form a seal. The stent may be coated with a polymeric material, for example, by immersion in molten polymer or any other method known to one of skill in the art. The stent may be located on the exterior of the device, the interior of the device, or both. A stent may be self-expanding, balloon-expandable or may have characteristics of both. A variety of other stent configurations are also contemplated by the use of the term "stent."

The term "graft or graft material" describes an object, device, or structure that is joined to or that is capable of being joined to a body part to enhance, repair, or replace a portion or a function of that body part. A graft by itself or with the addition of other elements, such as structural components, can be an endoluminal prosthesis. The graft comprises a single material, a blend of materials, a weave, a laminate, or a composite of two or more materials. The graft can also comprise polymer material that may be layered onto the mandrel of the present invention. Preferably, polymers of the present invention, although added in layers onto the mandrel, after curing, result in one layer that encapsulates a stent or woven graft. This also aids in decreasing the incidence of delamination of the resulting endovascular prosthesis. A stent may be attached to a graft to form a "stent graft."

The term "monolithic" refers to or describes objects or structures that are formed form only one piece.

The present invention relates to a stent formed from a plurality of separate, individual stent units. Each individual strut segments, when not connected to another individual strut segments, includes at least two bends and at least one attachment mechanism. The individual stent units are a monolithic structure including an attachment mechanism at the first straight end of the strut segment, i.e., do not constitute separate structure from the individual stent unit. A method of manufacturing the stent is also provided.

FIG. 1 shows one embodiment of a circular stent 10 constructed from individual monolithic stent units 12. In this particular embodiment, the stent 10 contains 10 individual monolithic stent units. The number of individual monolithic stent units 12 used to construct the stent 10 depends largely on the size and nature of the desired stent 10. The desired diameter of a resulting stent may be determined based upon the diameter of the lumen into which the stent will be inserted.

In another embodiment, not shown, the stent 10 may include a plurality of individual monolithic stent units 12, where every other individual monolithic stent unit 12 has a different diameter than the preceding individual monolithic stent unit. The different strut diameters allow for the reduction of size of the stent 10 when it is collapsed for delivery due to the reduced overall diameter of the stent 10. Further, the different diameters of the individual monolithic stent units 12 strut segments may also allow one of ordinary skill in the art to altering the amount of outward force used when the device is deployed within the body of a patient. The diameters of the strut segments can range from about from 0.010 to about 0.022 inches.

Figure 2:
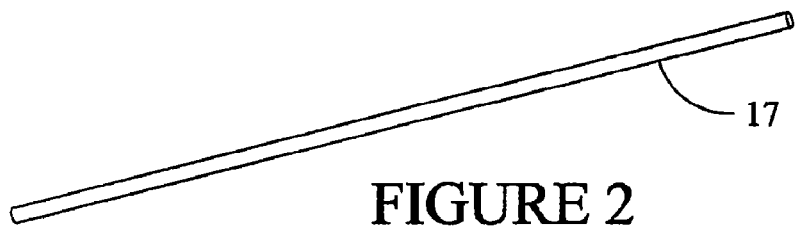
FIG. 2 shows an individual monolithic stent unit used to form the stent shown in FIG. 1, prior to formation into a bent individual monolithic stent unit.
Figure 3:
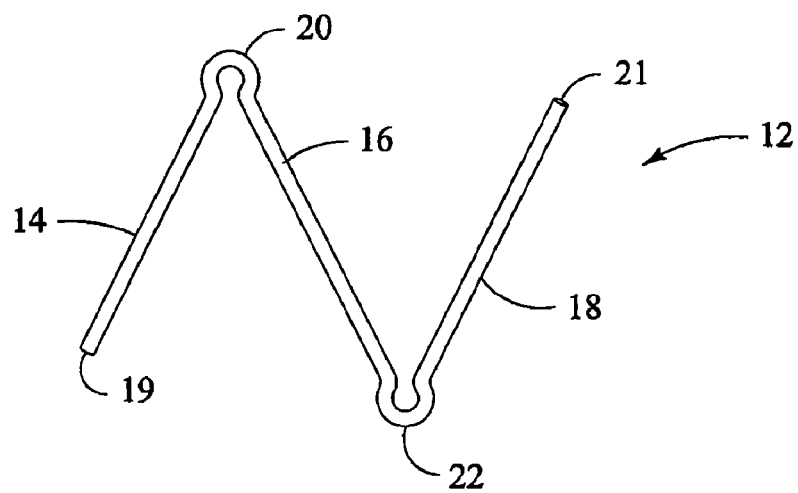
FIG. 3 shows an embodiment of an individual monolithic stent unit of FIG. 2 after having been bent into a generally undulating configuration.

The features of the stent 10 are best illustrated by a discussion of the method of manufacturing the stent 10. As shown in FIG. 2, each individual monolithic stent unit constitutes a single individual unit 17, such as an individual wire. Either or both of the ends of the wire 19, 21 may be sharpened or formed for use as an attachment mechanism (such as a hook or barb) for the resulting stent. Each individual monolithic stent unit may be provided with one or more bends. As shown in FIG. 3, an exemplary individual monolithic stent unit 12 has been bent twice (with two apices in opposing directions) such that the individual monolithic stent unit 12 forms a generally undulating shape have three struts 14, 16, 18. The first strut 14 is connected to the middle strut 16 at the first apex 20. The middle strut 16 is connected to the third strut 18 at the second apex 22. The apices may merely be bends or, as shown in FIG. 3, they may form partial eyelets or closed eyelets (not shown). The individual monolithic stent unit 12 is manufactured such that the distance between the first apex 20 and the second apex 22 is generally about 22 mm.

The individual monolithic stent units are each manufactured from biocompatible material. The materials used in the manufacture of the device may be selected from a well-known list of suitable metals. Preferred materials include those materials that can provide the desired functional characteristics with respect to mechanical load bearing, biological compatibility, modulus of elasticity, or other desired properties. In various embodiments, the stent includes a metallic material selected from stainless steel, nickel, silver, platinum, palladium, gold, titanium, tantalum, iridium, tungsten, cobalt, chromium, a nickel-titanium alloy, a superelastic nickel-titanium (NiTi) alloy sold under the trade name NITINOL® or inconel. Preferably, the individual monolithic stent units are manufactured from nitinol or stainless steel.

When using stainless steel wire, the size of the wire selected depends on the size of device and the application. An occlusion device, for example, preferably uses 0.010" wire for a 10 mm square frame, while 0.014" and 0.016" wire would be used for 20 mm and 30 mm frames, respectively. Wire that is too stiff can damage the vessel, not conform well to the vessel wall, and increase the profile of the device when loaded in the delivery system prior to deployment.

Figure 4:
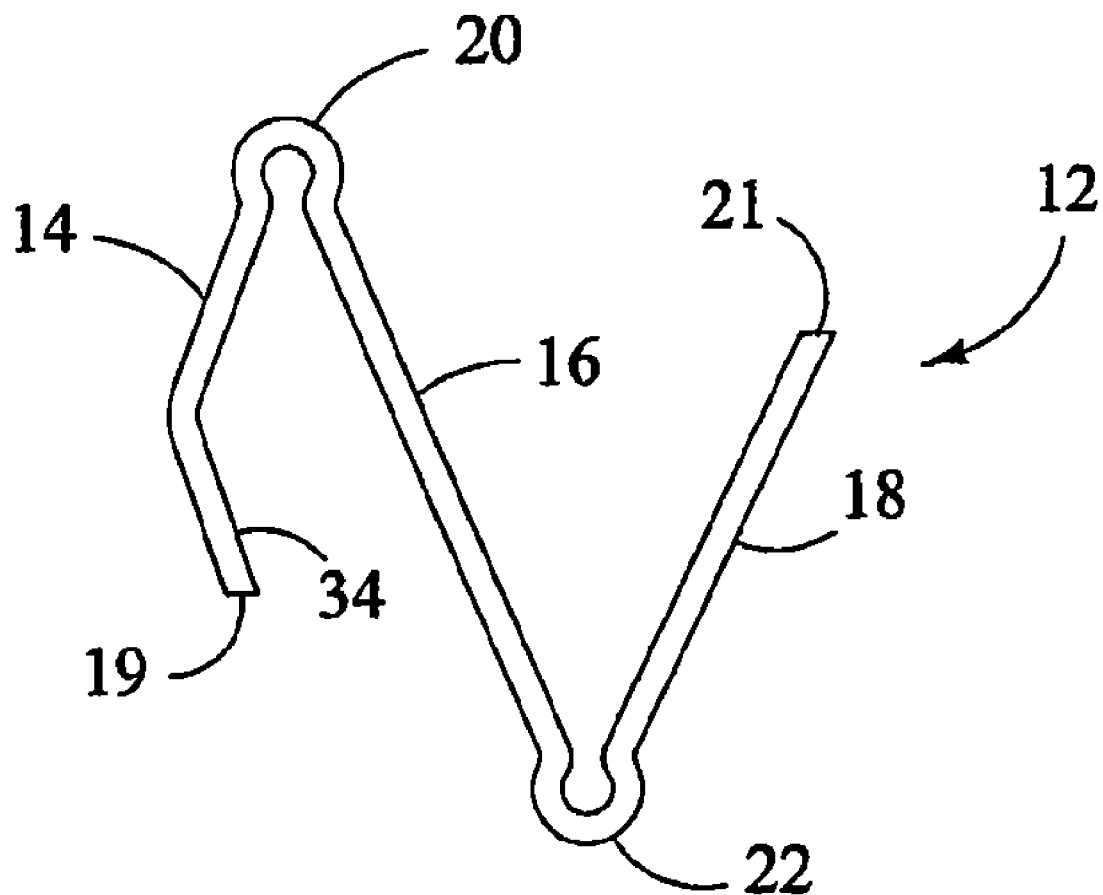
FIG. 4 shows an alternative embodiment of an individual monolithic stent unit of FIG. 2 after having been formed into a generally undulating configuration and having an attachment mechanism.

FIG. 4 illustrates an individual monolithic stent unit 12 including an attachment mechanism 34 at the end of the first strut 14. The attachment mechanism, or barb, will comprise the same material as the prosthesis, such as stainless steel, a nickel-titanium alloy, etc. The tip of the attachment mechanism may be ground to a sharpened point for better tissue penetration.

Figure 5:
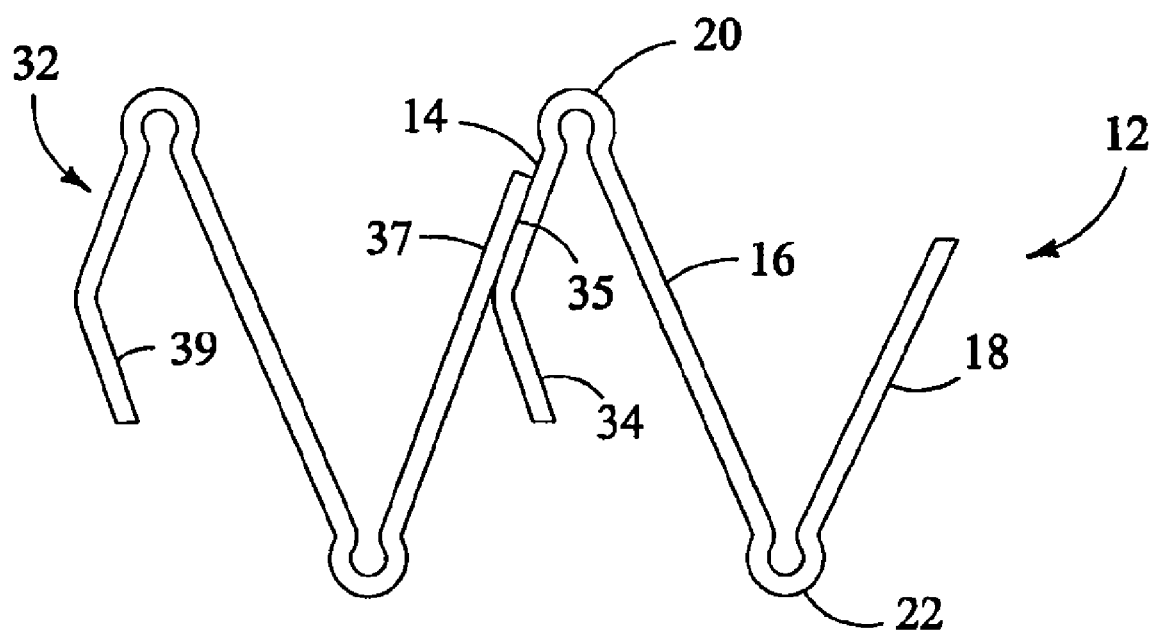
FIG. 5 shows two connected individual monolithic stent units of FIG. 4 used to form a stent joined together in accordance with the present invention.

Referring now to FIG. 5, two individual monolithic stent units 12 and 32 of an embodiment of the present invention are shown joined together. The two individual monolithic stent units 12 and 32 are joined together at attachment point 35. The attachment point 35 is formed between the first strut segment 14 of the individual monolithic stent unit 12 and the third strut segment 37 of individual monolithic stent unit 32. This attachment point 35 may be formed by many suitable methods including laser welding, soldering, brazing, and ultrasonic welding. Attachment mechanisms 34 and 39 are formed from the first strut segment of each individual monolithic stent unit 12 and 32. As shown in FIG. 5, the attachment mechanisms 34 and 39 are formed such that they generally face the distal direction with respect to individual monolithic stent segments 12 and 32, respectively. The angle formed by the attachment mechanisms 34 and 39 with respect to the individual monolithic stent units 12 and 32 ranges from between about 10° to about 20°. Preferably, the attachment mechanisms 34, 54 have an angle of about 15°.

Figure 6:
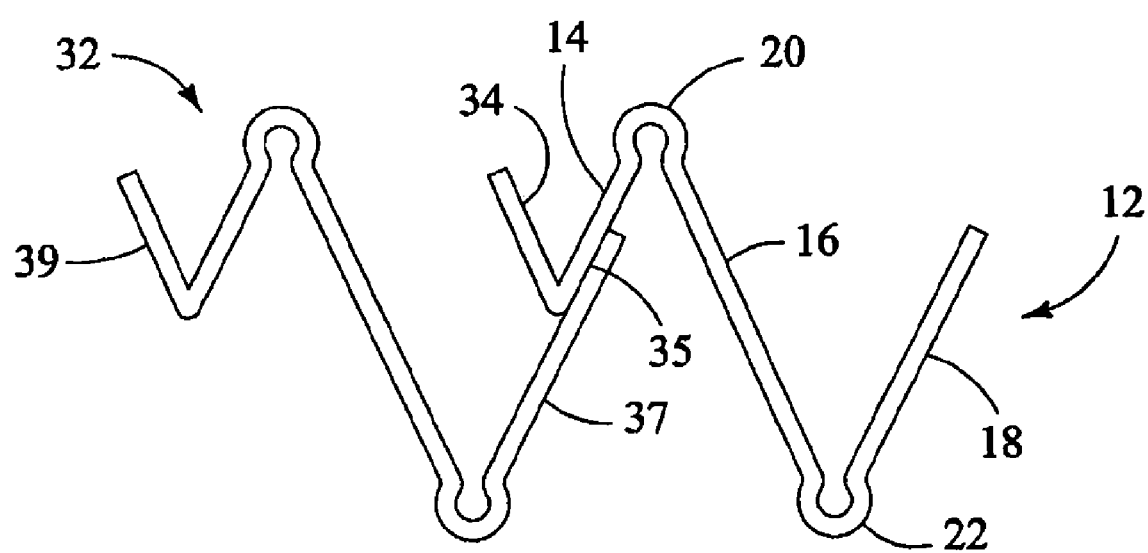
FIG. 6 shows an alternate embodiment of two connected individual monolithic stent units used to form a stent joined together in accordance with the present invention.
Figure 7:
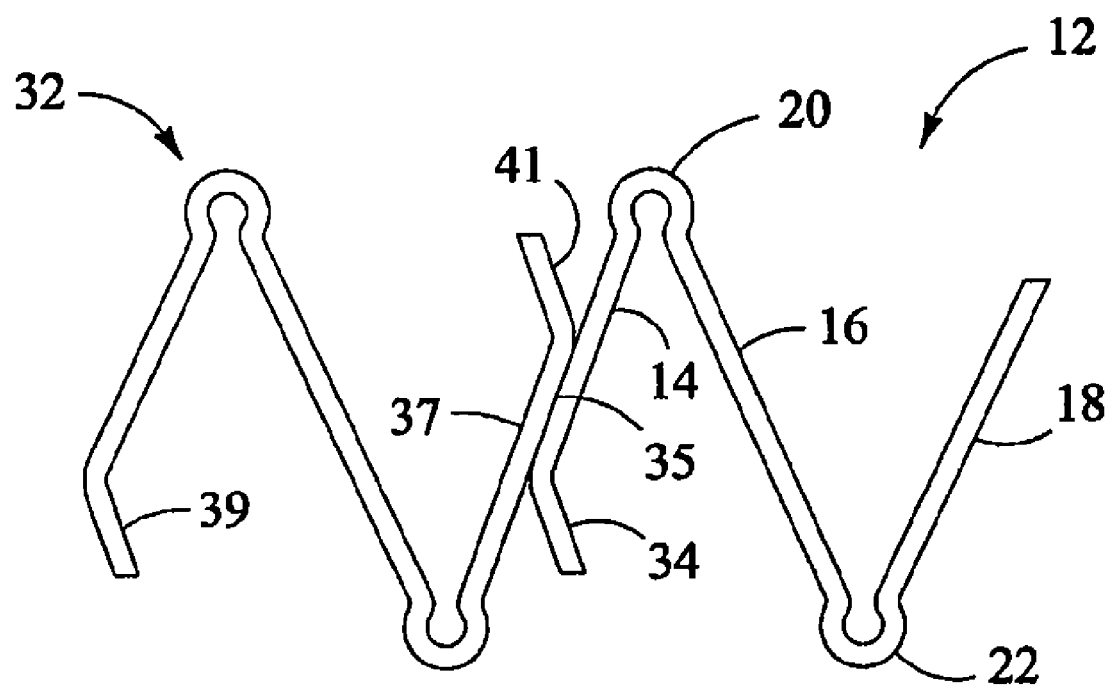
FIG. 7 shows an alternate embodiment of two connected individual monolithic stent units used to form a stent joined together in accordance with the present invention.

Alternatively, in another example, the attachment mechanism 34 may be formed such that it generally faces in the proximal direction with respect to individual stent segments 12 and 32, as shown in FIG. 6. In another example, an attachment mechanism 41 may be formed from the third strut segment 37, as well as from the first strut segment. As demonstrated by the embodiment in FIG. 7, the attachment mechanisms 34 and 39 are formed such that they face in the distal direction, while attachment mechanism 41 is formed such that it generally faces the proximal direction. Attachment point 35 is formed at a predetermined distance between attachment mechanisms 34 and 41 so as to minimize the amount of stress on the two attachment mechanisms.

Figure 8:
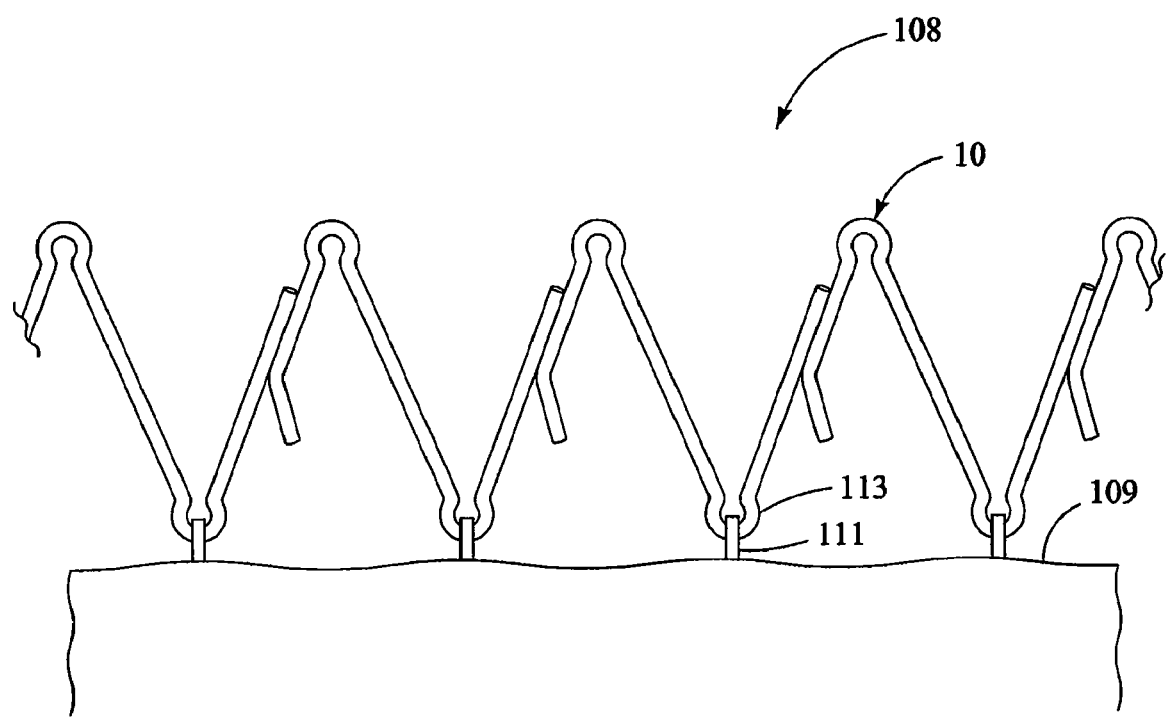
FIG. 8 shows an embodiment of a stent of the present invention attached to graft material in accordance with the present invention.

The stent 10 may be attached to graft material to form the endoluminal device 108. FIG. 8 illustrates the attachment of the stent 10 to graft material 109. The graft material 109 may be attached to the stent by any appropriate attachment means, including but not limited to stitching using sutures, adhesive, fasteners, and tissue welding using heat and/or pressure. Suture material may be polypropylene or any other suitable material known in the art. In the example as shown in FIG. 8, the graft material 109 is affixed to the stent 10 using sutures 11 that are threaded through the distal apex 113 of the stent 10.

The graft material may be constructed from a biocompatible textile fabric, a polymer, biomaterial, or a composite thereof. Examples of biocompatible materials from which textile graft material can be formed include polyesters, such as polyethylene terephthalate; fluorinated polymers, such as polytetrafluoroethylene (PTFE) and fibers of expanded PTFE; and polyurethanes. Preferably, the graft material is a woven polyester. More preferably, the graft material is a polyethylene terephthalate (PET), such as DACRON® (DUPONT, Wilmington, Del.) or TWILLWEAVE MICREL® (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids. The woven polyester of the graft material may comprise a plurality of yarns.

Figure 9:
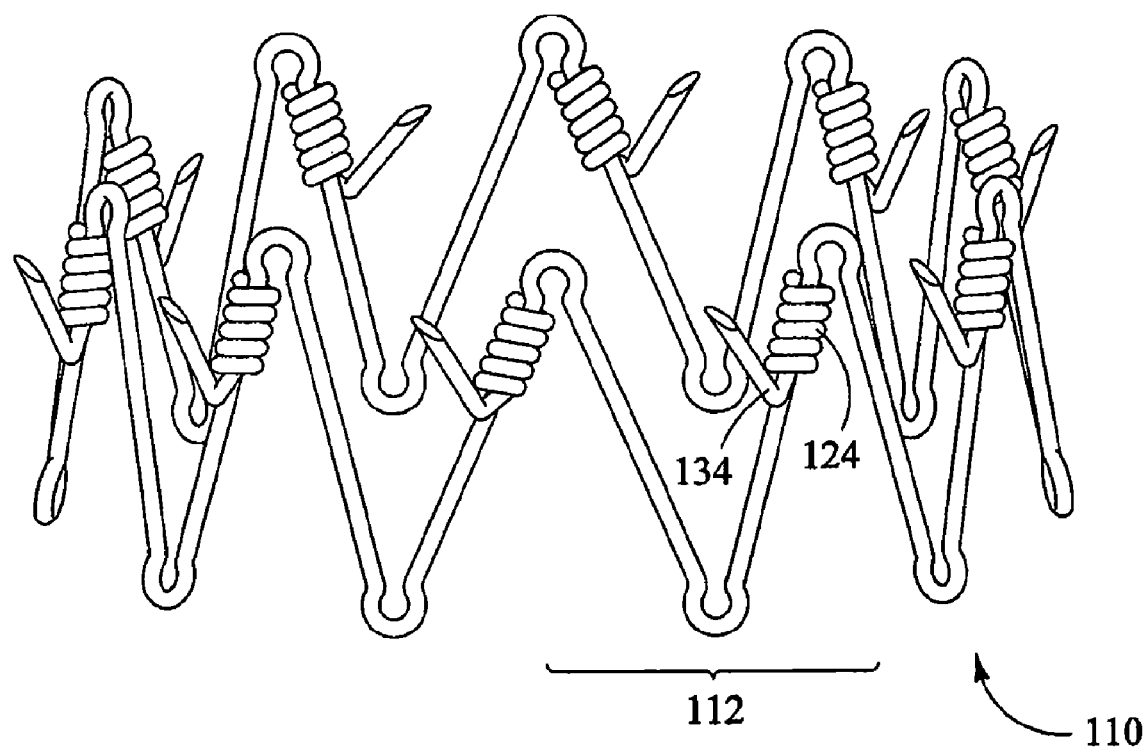
FIG. 9 shows an embodiment of a generally circular stent constructed from individual monolithic stent units according to the present invention.

FIG. 9 shows another embodiment of a circular stent constructed from individual monolithic stent units. As shown, the stent 110 is construed of a number (nine in FIG. 9) individual stent 110 monolithic stent units 112 that have been bent into a particular configuration and mechanically attached to one another without soldering or adhesive to form a stent ring. The number of individual monolithic stent units depends largely on the size and nature of the desired stent. The desired diameter of a resulting stent may be determined based upon the diameter of the lumen into which the stent will be inserted.

Figure 10:
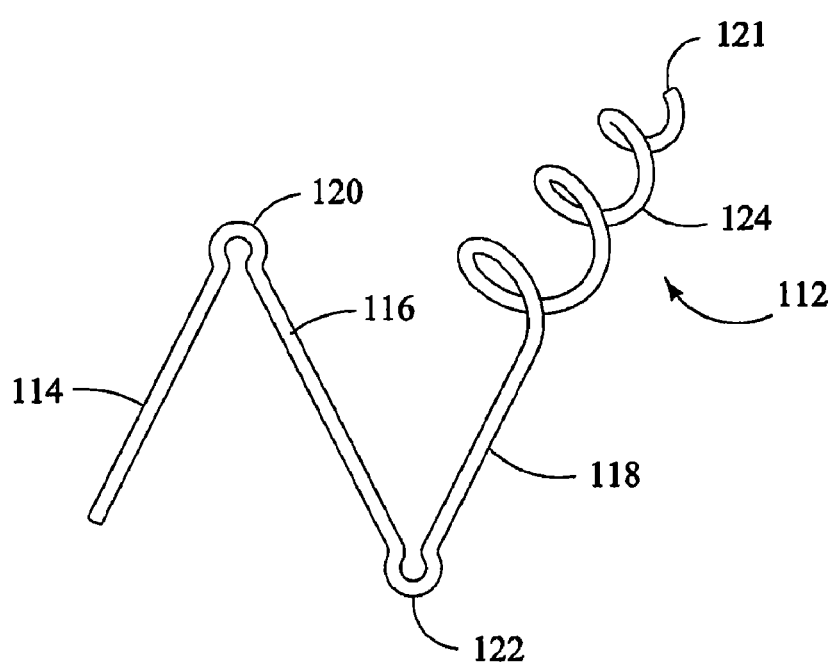
FIG. 10 shows an alternative embodiment of an individual monolithic stent unit of FIG. 2 used to form a stent where an end of the wire being formed into a coil.
Figure 11:
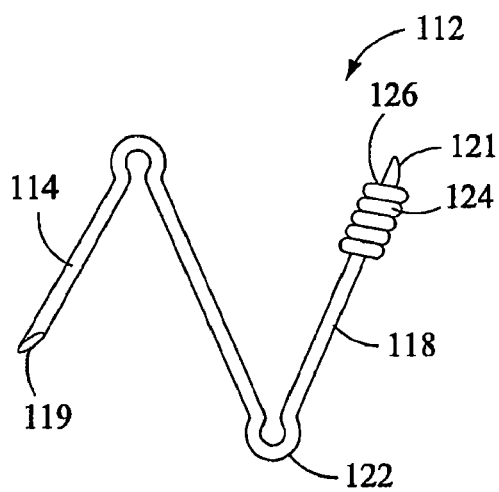
FIG. 11 shows the individual monolithic stent unit of FIG. 3 where a coil has been formed in the wire near the end of the wire.

FIG. 10 shows an individual monolithic stent unit 112 in which one end 121 of the individual monolithic stent unit 112 is being formed into a coil 124. FIG. 11 shows the individual monolithic stent unit after the coil 124 has been formed. The coil 124 has lumen 126. Lumen 126 should be sized to accommodate a wire roughly of the gauge of the wire forming the coil.

Figure 12:
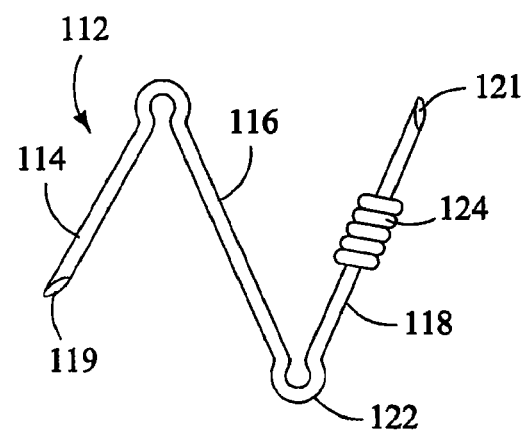
FIG. 12 shows an embodiment of the individual monolithic stent unit of FIG. 3 where the coil is located substantially in the middle of the portion of the wire in which it is disposed.

As shown in FIG. 11, the coil 124 may formed at the end of strut 118, or, as shown in FIG. 12, the coil may be formed away from the end of the strut 118. For example, as shown in FIG. 12, coil 124 is located approximately equidistant between apex 122 and end 121. As shown in FIGS. 11 and 12, either or both ends (119 and 121) may be sharpened into a sharp point.

Figure 13:
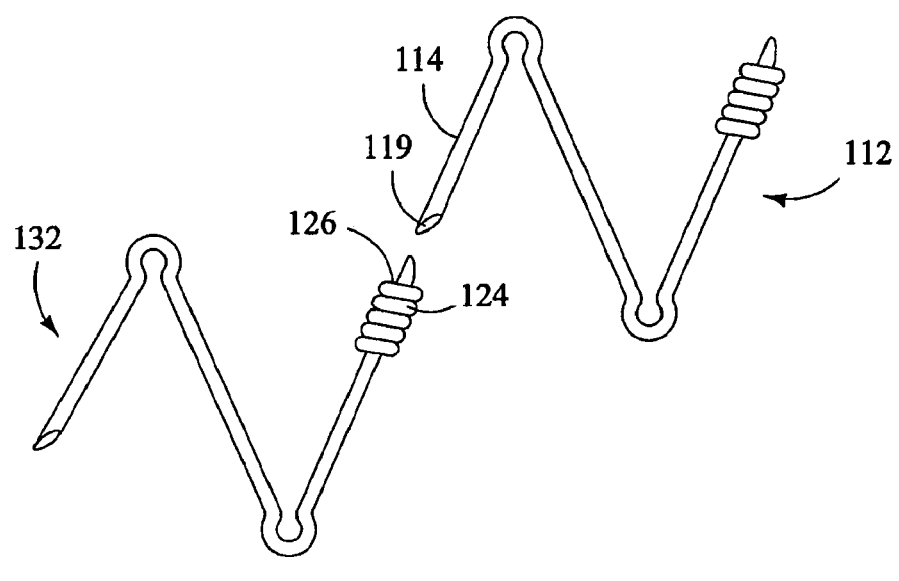
FIG. 13 shows two individual monolithic stent units used to form a stent just prior to inserting the barb end of one individual monolithic stent unit into the lumen of a coil of the other individual monolithic stent unit.
Figure 14:
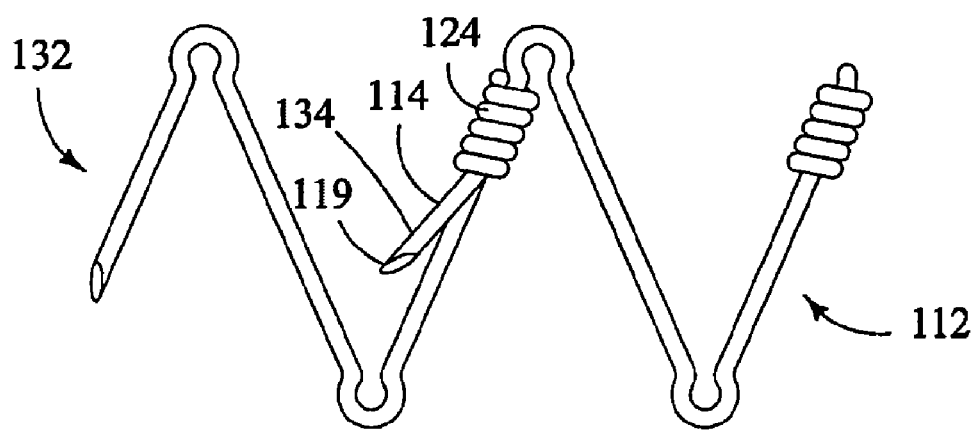
FIG. 14 shows two connected individual monolithic stent units after the barb section of one individual monolithic stent unit has been inserted into the lumen of the coil of the second individual monolithic stent unit.

Two individual monolithic stent units 112 and 132 may then be joined together as shown in FIG. 13. For example, the first end 119 of the stent unit 112 may be inserted into the lumen 126 of the coil 124 of stent unit 132, such that the end 119 of stent unit 112 passes through the lumen 126 of coil 124 of stent unit 132. Desirably, end 119 of stent unit 112 protrudes some length from lumen 126. As shown in FIG. 14, the first end 119 of the stent unit 112 is inserted through the lumen 126 and extends through the coil 124. End 119 may then form an attachment mechanism 134.

Figure 15:
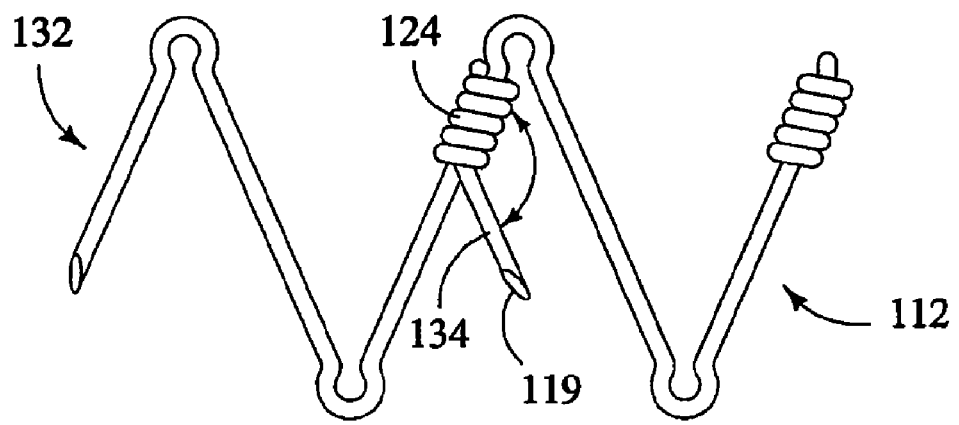
FIG. 15 shows two connected individual monolithic stent units after the barb section of one individual monolithic stent unit has been inserted into the lumen of the coil of the second individual monolithic stent unit and the barb section is bent such that the angle between the barb section and the coil is obtuse.
Figure 16:
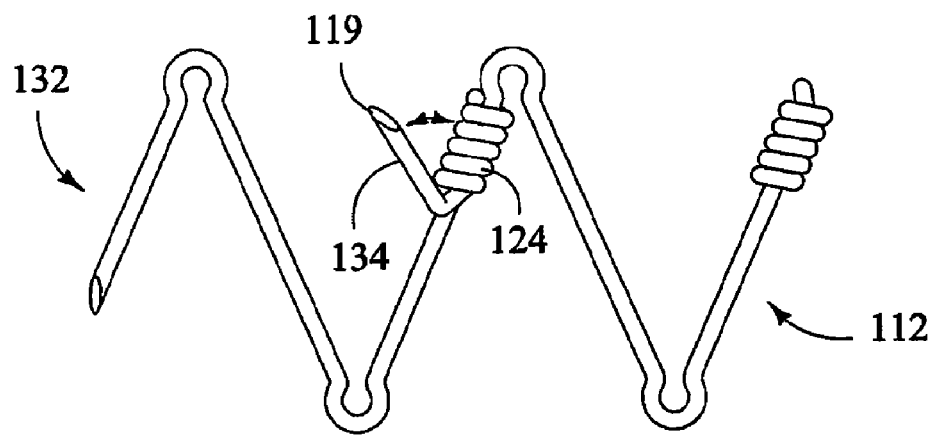
FIG. 16 shows two connected individual monolithic stent units after the barb section of one individual monolithic stent unit has been inserted into the lumen of the coil of the second individual monolithic stent unit and the barb section is bent such that the angle between the barb section and the coil is acute.

The attachment mechanism 134 may then be bent to form an angle with regard to the axis of the coil. Bending the attachment mechanism locks the individual monolithic stent units 112 and 132 together and prevents them from sliding apart. In one example, the attachment mechanism 134 may be bent such that an obtuse angle is formed between the coil 124 and the attachment mechanism 134 as shown in FIG. 15. In another example, the attachment mechanism 134 may be bent such that an acute angle is formed between the coil 124 and the attachment mechanism 134 as shown in FIG. 16. Bending the attachment mechanism to form an acute angle may reduce movement and provide more security in joining the two stent units 112, 132. Whether an acute or obtuse angle is formed largely depends on how the stent is used. For example, if the stent is used at the proximal end of a stent graft (nearest the heart) in a stent graft designed to exclude an aneurysm, an obtuse angle (with the attachment points facing distally or in the direction of the blood flow) may be desirable.

Figure 17:
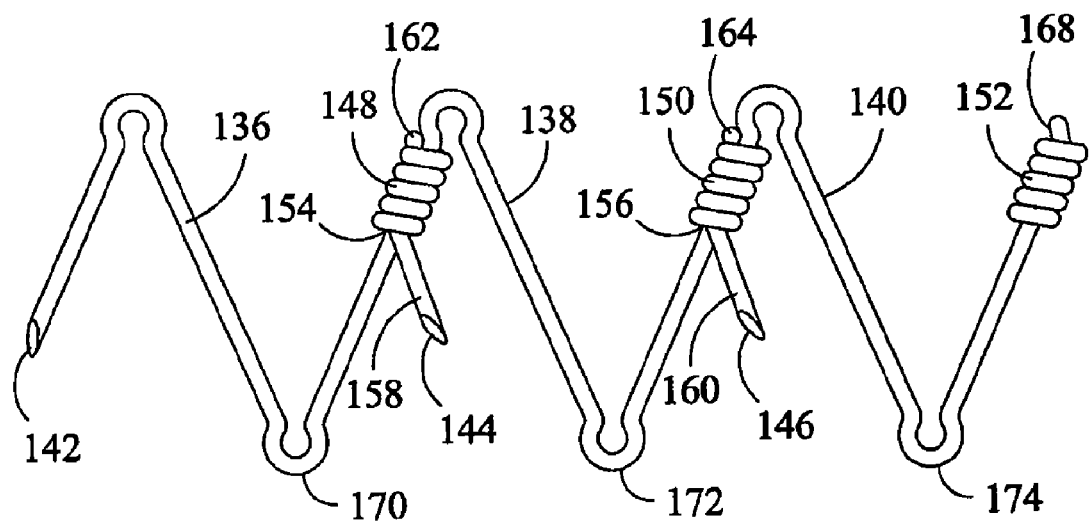
FIG. 17 shows multiple connected individual monolithic stent units where the angle between the barb section and the coil is obtuse.

FIG. 17 illustrates three individual monolithic stent units 136, 138, 140 joined together. In this example, the end 146 of individual monolithic stent unit 140 is inserted into the lumen 156 of coil 150 of adjacent individual monolithic stent unit 138. The end 144 of individual monolithic stent unit 138 is inserted into the lumen 154 of coil 148 of the adjacent individual monolithic stent unit 136. Attachment mechanism 158 is bent such that an obtuse angle is formed between the coils 148 and the attachment mechanism 158. Similarly, attachment mechanism 160 is bent such that an obtuse angle is formed between the coils 150 and the attachment mechanism 160. As shown, coil 152 of individual monolithic stent unit 140 is positioned nearer to the end 168 than to apex 174. Similarly, coil 148 of individual monolithic stent unit 136 is positioned nearer to the end 162 than to apex 170 and coil 150 of individual monolithic stent unit 138 is positioned nearer to the end 164 than to apex 172.

Figure 18:
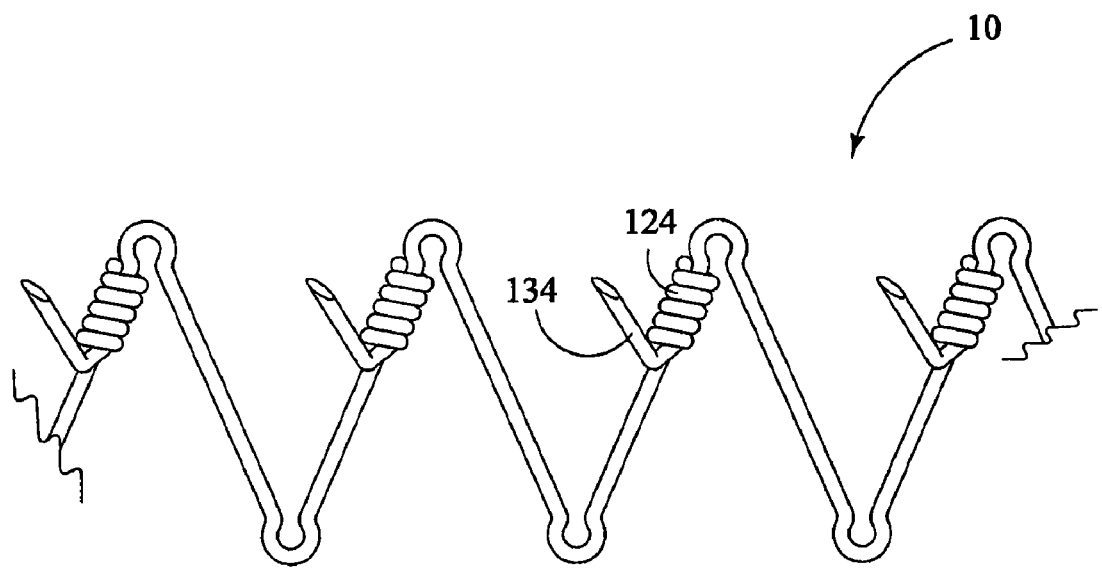
FIG. 18 shows three connected individual monolithic stent units where the angle between the barb section and the coil is acute.

In another example, as shown in FIG. 18, several individual monolithic stent units are joined together. Each of the attachment mechanisms 134 are bent such that an acute angle is formed between the coil 124 and the attachment mechanism 134. In each of the examples as shown in FIGS. 17 and 18, each of the attachment mechanisms are bent to form substantially the same angle between the attachment mechanism and the coil.

Figure 19:
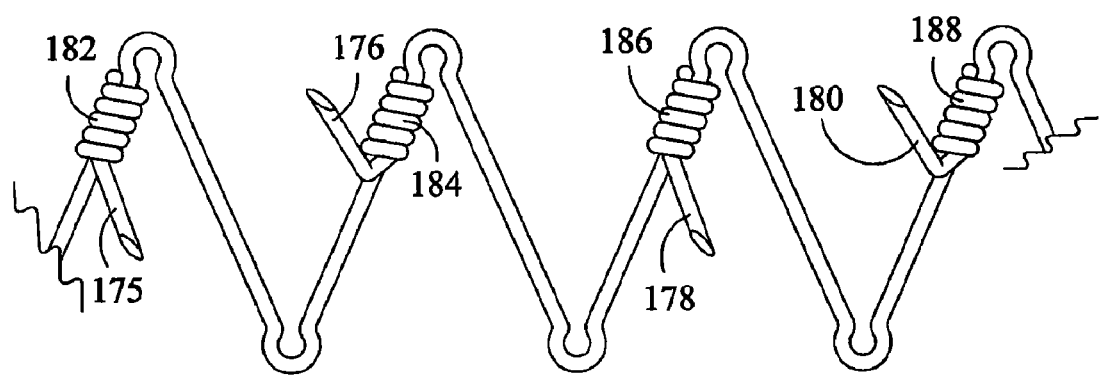
FIG. 19 shows multiple connected individual monolithic stent units where the angle between the barb section and the coil where the angle between the barb section and the coil alternates between obtuse and acute.

In another example, attachment mechanisms on different units may be bent differently. For example, the attachment mechanism of one monolithic stent unit may be bent at an obtuse angle whereas an attachment mechanism on a neighboring or other unit may be bent at an acute angle. FIG. 19 shows a stent where every other attachment mechanism is bent to form an acute angle between the coil and the attachment mechanism and each additional attachment mechanism is bent to form an obtuse angle between the coil and attachment mechanism. Specifically, attachment mechanisms 175 and 178 are bent to form an obtuse angle between the attachment mechanisms 175 and 178 and the coils 182 and 186, respectively. Attachment mechanisms 176 and 180 are bent to form an acute angle between the attachment mechanisms and the coils 184 and 188, respectively.

Figure 20:
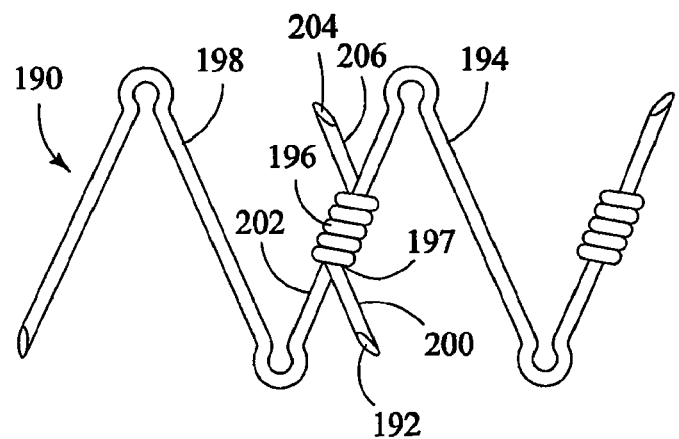
FIG. 20 shows a stent where the coil in the first section is formed in the middle of the strut of the first individual monolithic stent unit and the barb section of a second individual monolithic stent unit has been inserted into the lumen of the coil of the first section, and where both the barb section of the section individual monolithic stent unit and the uncoiled end of the first individual monolithic stent unit adjacent the coil form attachment barbs.

In another example as shown in FIG. 20, the stent 190 is made up of individual monolithic stent units bent into a configuration as shown in FIG. 11, where the individual monolithic stent unit 112 is bent such that the coils are placed such that coil 124 is located approximately equidistant between apex 122 and end 121. In this example, the first end 192 of the first individual monolithic stent unit 194 extends through the lumen 197 of coil 196 of the second individual monolithic stent unit 198 to form an attachment mechanism 200. Because the coil 196 is disposed in the middle of the middle strut 202 of the second monolithic stent unit 198, the second end 204 of the second individual monolithic stent unit 198 forms a second attachment mechanism 206 adjacent to the coil 196. In this example, obtuse angles are formed between the coil 196 and each attachment mechanism 200, 206.

Figure 21:
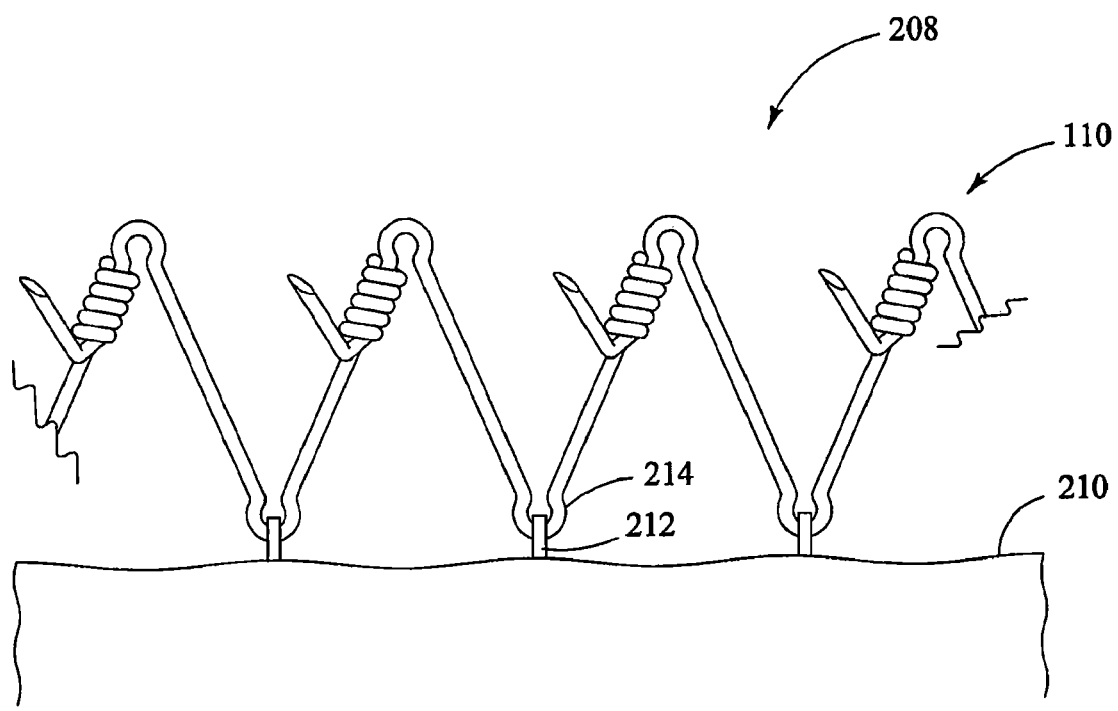
FIG. 21 shows a stent formed of a series of individual monolithic stent units attached to graft material.

The stent 110 may be attached to graft material to form the endoluminal device 208. FIG. 21 shows attachment of the stent 110 to graft material 210. The graft material may be attached to the stent by any appropriate attachment means, including but not limited to stitching using sutures, adhesive, fasteners, and tissue welding using heat and/or pressure. Suture material may be polypropylene or any other suitable material known in the art. In the example as shown in FIG. 21, the graft material 210 is affixed to the stent 110 using sutures 212, which are threaded through the apex 214 of the stent.

The endoluminal device 108, 208 may be delivered and positioned in the body vessel using methods known in the art. For example, the device may be loaded into a delivery device, such as a catheter. The device may be mounted within a retaining sheath that contacts the outer surface of the stent and retains the stent in a compressed state for delivery into a vessel. A hollow needle may be used to penetrate the vessel, and a guide wire may be threaded through the needle into the vessel. The needle may then be removed and replaced with an introduction catheter, which generally acts as a port through which endoluminal devices, including stents, may then be passed to gain access to a vessel. The compressed stent and the retaining sheath may then be passed through the introduction catheter into the vessel. Once the stent is positioned within the vessel adjacent to the site to be treated, the retaining sheath may be retracted, thereby causing the stent to expand from the compressed state to an expanded state. In the expanded state, the stent contacts and exerts a radial force on the vessel wall. The retaining sheath and the introduction catheter may then be withdrawn from the vessel.

It is therefore intended that the foregoing detailed description be regarded as illustrative rather than limiting, and that it be understood that it is the following claims, including all equivalents, that are intended to define the spirit and scope of this invention.

We claim:

1. A stent, comprising:
   at least two individual stent units,
   each stent unit comprising, as a monolithic structure:
   a first strut,
   a second strut,
   and a third strut,
   a first apex adjoining the first and second struts,
   a second apex adjoining the second and third struts, where the second apex is disposed in a direction generally opposite the first apex; and
   an attachment mechanism at an end of at least the first strut; and
   where the first strut of each monolithic stent unit is joined at an attachment point to the third strut of an adjacent monolithic stent unit;
   where the attachment mechanism is bent to form an angle relative to the attachment point; and
   where the attachment mechanism is adjacent to the attachment point.

2. The stent of claim 1, where the third strut of the monolithic stent unit comprises a coiled attachment point.

3. The stent of claim 2, where each attachment mechanism of each monolithic stent unit is passed through an end of the coil lumen of an adjacent monolithic stent unit to join with an adjacent monolithic stent unit, such that the attachment mechanism of the first monolithic stent unit is passed through the coil lumen of the last monolithic stent unit to form an annular stent; and
   where each attachment mechanism exits from the coil at the other end of the coil lumen and is bent to form an angle relative to the longitudinal axis of the coil.

4. The stent of claim 2, where the coil of the monolithic stent unit is disposed substantially equidistant between the second apex and an end of the third strut.

5. The stent of claim 1, where the monolithic stent unit further comprises an attachment mechanism at an end of the third strut.

6. The stent of claim 1, where the first strut of each individual monolithic stent unit is directly interconnected with the third strut of an adjacent individual monolithic stent unit.

7. The stent of claim 6, where the first strut of each individual monolithic stent unit and the third strut of an adjacent individual monolithic stent unit are interconnected by laser welding, brazing, soldering, or ultrasonic welding.

8. The stent of claim 1, where the diameter of each individual monolithic stent unit ranges from about 0.014" to about 0.022".

9. The stent of claim 1, where the amount of individual monolithic stent units in the stent ranges from about 10 individual monolithic stent units to 18 individual monolithic stent units.

10. The stent of claim 1 comprising at least two or more of the following:
    where the third strut of the monolithic stent unit comprises a coiled attachment point;

where the third strut of the monolithic stent unit comprises a coiled attachment point, and where each attachment mechanism of each monolithic stent unit is passed through an end of the coil lumen of an adjacent monolithic stent unit to join with an adjacent monolithic stent unit, such that the attachment mechanism of the first monolithic stent unit is passed through the coil lumen of the last monolithic stent unit to form an annular stent, exits from the coil at the other end of the coil lumen, and is bent to form an angle relative to the longitudinal axis of the coil;

where the third strut of the monolithic stent unit comprises a coiled attachment point disposed substantially equidistant between the second apex and an end of the third strut;

where the monolithic stent unit structure comprising an attachment mechanism at an end of the third strut;

where the first strut of each individual monolithic stent unit is directly interconnected with the third strut of an adjacent individual monolithic stent unit;

where the first strut of each individual monolithic stent unit and the third strut of an adjacent individual monolithic stent unit are interconnected by laser welding, brazing, soldering, or ultrasonic welding;

where the amount of individual monolithic stent units in the stent ranges from about 10 individual monolithic stent units to 18 individual monolithic stent units; or where the diameter of each individual monolithic stent unit ranges from about 0.014" to about 0.022".

11. A stent, comprising: a series of at least two individual stent units including a first stent unit and a last stent unit in the series of stent units, each stent unit comprising as a monolithic structure:

a first strut, a second strut, and a third strut, a first apex adjoining the first and second struts, a second apex adjoining the second and third struts, where the second apex is disposed in a direction generally opposite the first apex; and an attachment mechanism at an end of the first strut;

where the first strut of each monolithic stent unit is joined at an attachment point to the third strut of an adjacent monolithic stent unit;

where the third strut comprises a coiled attachment point with a coil and a coil lumen, and each attachment mechanism of each monolithic stent unit is passed through an end of the coil lumen of an adjacent monolithic stent unit to join with an adjacent monolithic stent unit, such that the attachment mechanism of the first monolithic stent unit is passed through the coil lumen of the last monolithic stent unit to form an annular stent; and where each attachment mechanism exits from the coil at the other end of the coil lumen and is bent to form an angle relative to the longitudinal axis of the coil; and where the attachment mechanism is adjacent to the attachment point.

12. The stent of claim 11, where the first strut of each individual monolithic stent unit and the third strut of an adjacent individual monolithic stent unit are interconnected by laser welding, brazing, soldering, or ultrasonic welding.

13. The stent of claim 11, where the coil of the monolithic stent unit is disposed substantially equidistant between the second apex and an end of the third strut.

14. The stent of claim 11, where the monolithic stent unit further comprises an attachment mechanism at an end of the third strut.

15. A method of forming a stent from a series of separate and individual monolithic stent units comprising:

providing at least two individual monolithic stent units;

bending each of the monolithic stent units to form a configuration having three struts, a first strut, a second strut, and a third strut, where a first apex adjoins the first and second struts and a second apex adjoins the second and third struts, where the second apex is disposed in a direction generally opposite the first apex;

attaching a portion of the first strut of each monolithic stent unit to the third strut of an adjacent monolithic stent unit to join with the adjacent monolithic stent unit to form an attachment mechanism;

bending each attachment mechanism to form an angle relative to the longitudinal axis of the second strut.

16. The method of claim 15, further comprising forming a coil into the third strut.

17. The method of claim 16, further comprising inserting a portion of the first strut of each individual monolithic stent unit through the coil lumen of an adjacent monolithic stent unit to join with the adjacent monolithic stent unit to form an attachment mechanism.

18. The method of claim 17, further comprising bending each attachment mechanism to form an angle relative to the longitudinal axis of the coil.

19. The method of claim 15, further comprising interconnecting the first strut of each individual monolithic stent unit and the third strut of an adjacent individual monolithic stent unit by laser welding, brazing, soldering, or ultrasonic welding.

* * * * *